US012622790B2

(12) United States Patent     (10) Patent No.: US 12,622,790 B2

Liauw et al.     (45) Date of Patent: May 12, 2026

(54) INTERVERTEBRAL FUSION DEVICE WITH BONE GRAFT LUMBAR

(71) Applicant: BLOOM BIOMEDICAL, INC., Irvine, CA (US)

(72) Inventors: Jason Liauw, Irvine, CA (US); Nicholas Hu, Irvine, CA (US)

(73) Assignee: Bloom Biomedical, Inc., Irvine, CA (US)

( * ) Notice: Subject to any disclaimer, the term of this patent is extended or adjusted under 35 U.S.C. 154(b) by 308 days.

(21) Appl. No.: 18/246,370

(22) PCT Filed: Sep. 23, 2021

(86) PCT No.: PCT/US2021/051829

§ 371 (c)(1),
(2) Date: Mar. 23, 2023

(87) PCT Pub. No.: WO2022/066962

PCT Pub. Date: Mar. 31, 2022

(65) Prior Publication Data

US 2023/0363928 A1    Nov. 16, 2023

Related U.S. Application Data

(60) Provisional application No. 63/172,945, filed on Apr. 9, 2021, provisional application No. 63/082,255, filed on Sep. 23, 2020.

(51) Int. Cl.
| | |
|---|---|
| *A61F 2/46* | (2006.01) |
| *A61F 2/30* | (2006.01) |
| *A61F 2/44* | (2006.01) |

(52) U.S. Cl.
CPC .............. *A61F 2/4611* (2013.01); *A61F 2/30* (2013.01); *A61F 2/4455* (2013.01); *A61F 2002/30537* (2013.01)

(58) Field of Classification Search
CPC ........ A61F 2/4611; A61F 2/30; A61F 2/4455; A61F 2/46; A61F 2002/30537
See application file for complete search history.

(56) References Cited

U.S. PATENT DOCUMENTS

| | | | |
|---|---|---|---|
| 5,571,189 | A | 11/1996 | Kuslich |
| 6,383,188 | B2 | 5/2002 | Kuslich et al. |
| 6,582,467 | B1 | 6/2003 | Teitelbaum et al. |

(Continued)

FOREIGN PATENT DOCUMENTS

| | | |
|---|---|---|
| CA | 2456365 A1 | 8/2004 |
| JP | 2006517842 A | 8/2006 |

(Continued)

OTHER PUBLICATIONS

International Search Report and Written Opinion received in International Application No. PCT/US2021/051829, mailed on Feb. 18, 2022, 15 pages.

(Continued)

*Primary Examiner* — Eduardo C Robert
*Assistant Examiner* — Holly Joanna Lane
(74) *Attorney, Agent, or Firm* — Perkins Coie LLP

(57) ABSTRACT

Described herein are intervertebral fusion devices and their methods of use. Also described herein are interbody device systems and the methods of using the same.

27 Claims, 15 Drawing Sheets

(56)                References Cited

U.S. PATENT DOCUMENTS

| | | | |
|---|---|---|---|
| 6,666,891 B2 | 12/2003 | Boehm et al. | |
| 7,025,771 B2 | 4/2006 | Kuslich et al. | |
| 7,442,210 B2 | 10/2008 | Segal et al. | |
| 7,959,683 B2 | 6/2011 | Semler et al. | |
| 8,702,716 B1 * | 4/2014 | Stein | A61B 17/8836 606/94 |
| 8,906,094 B2 | 12/2014 | Roche et al. | |
| 9,387,088 B2 | 7/2016 | Roche et al. | |
| 2001/0056302 A1 * | 12/2001 | Boyer, II | B29C 43/006 623/17.15 |
| 2004/0106999 A1 * | 6/2004 | Mathews | A61M 25/10 606/279 |
| 2004/0133280 A1 | 7/2004 | Trieu | |
| 2004/0230309 A1 * | 11/2004 | DiMauro | A61F 2/441 623/17.11 |
| 2005/0055027 A1 * | 3/2005 | Yeung | A61B 17/0644 606/75 |
| 2006/0085073 A1 | 4/2006 | Raiszadeh | |
| 2006/0122621 A1 * | 6/2006 | Truckai | A61B 17/8822 606/93 |
| 2009/0088788 A1 * | 4/2009 | Mouw | A61B 17/025 606/192 |
| 2012/0165940 A1 | 6/2012 | Sennett et al. | |
| 2012/0215229 A1 | 8/2012 | Garcia-Bengochea et al. | |
| 2012/0277862 A1 | 11/2012 | Tornier et al. | |
| 2013/0310878 A1 | 11/2013 | McCormack et al. | |
| 2015/0202052 A1 | 7/2015 | Dimauro | |
| 2016/0022333 A1 | 1/2016 | Rabiner et al. | |
| 2018/0028200 A1 | 2/2018 | O'Neil et al. | |
| 2018/0256144 A1 | 9/2018 | O'Neil et al. | |
| 2019/0254714 A1 | 8/2019 | Greenhalgh et al. | |
| 2020/0054215 A1 * | 2/2020 | Roche | A61B 5/4504 |
| 2020/0375643 A1 | 12/2020 | Bjork et al. | |
| 2021/0085341 A1 | 3/2021 | Gleason et al. | |

FOREIGN PATENT DOCUMENTS

| | | |
|---|---|---|
| JP | 2019510549 A | 4/2019 |
| WO | 2022066962 A1 | 3/2022 |

OTHER PUBLICATIONS

International Search Report from PCT/US2024/021808 dated Aug. 21, 2024 (4 pgs).

"Extended European Search Report", from PCT/US2021051829 dated Oct. 2, 2024., Oct. 2, 2024, 1~8.

European Patent Office, Extended European Search Report from PCT/US2021051829, dated Oct. 2, 2024, 8 pages.

* cited by examiner

Mesh

Collapsed Structure

Hydraulic

Bone Graft Fill 100    102

302                    302'

INTERVERTEBRAL FUSION DEVICE WITH BONE GRAFT LUMBAR

CROSS REFERENCE TO RELATED APPLICATIONS

This application claims the benefit of U.S. Provisional Patent Application Ser. No. 63/082,255, filed Sep. 23, 2020, and U.S. Provisional Patent Application Ser. No. 63/172, 945, filed Apr. 9, 2021, the entire disclosures of each of which are incorporated herein by reference.

FIELD

Described herein are intervertebral fusion devices and their methods of use. Also, described herein are interbody systems and the methods of using the same.

BACKGROUND

Degenerative joint disease in the spine usually involves the tandem degeneration of the intervertebral disc and the two posterior facet joints which act as a tripod to provide stabilization between the vertebrae of the spine. Degeneration of these joints are respectively termed disc degenerative disease (DDD) or disc arthropathy, and facet degenerative disease or facet arthropathy. The result of DDD is often thinning of the disc and a collapse of the disc height. The openings through which the spinal nerve roots go through when leaving the spinal column are called neural foramen, and the height of these foramina directly correspond to the height of the intervertebral disc. With collapse of the intervertebral disc height, the natural height of the neural foramina also collapses and as a result the exiting nerve root is compressed which can elicit nerve pain or radicular pain down the legs. Along with that, intervertebral disc height collapse can cause ligamentous laxity and bulging in the spine. These ligaments, namely the posterior longitudinal ligament (PLL) and ligamentum flavum, surround the cord and can bulge into the spinal canal as the disc height collapses. The result is compression of the whole spinal cord or thecal sac centrally in the spinal canal which can result in radicular pain down the legs in addition to weakness and fatigue in the legs, termed neurogenic claudication.

The surgical treatment of back pain and sciatic pain include etiologies of pain which all stem from disc degenerative joint disease in the spine. These are as follows:

The treatment of mechanical instability of the spine: Mechanical instability is a result of degeneration of both the intervertebral disc and/or the posterior facet joints. The mechanical instability causes painful arthritic pain or arthropathy. Much of spinal fixation is geared toward reducing mechanical instability and thereby reducing the movement of arthritic joints that get inflamed with movement. There are numerous methods to accomplishing spinal fixation, with both anterior column and posterior column fixation devices. The most pervasive spinal fixation method to this day involves posterior screws used in combination with interbody cages for anterior column support.

The treatment of nerve root compression: As described above, nerve root compression can occur centrally around the spinal cord or thecal sac, or laterally around the exiting nerve root at the neural foramen. Pain from nerve root compression often travels according to a nerve root dermatomal distribution, causing radicular or sciatic pain. Spinal surgical decompression, aims to remove nerve pain by taking the compression off the nerve roots. This can be accomplished directly through removal of bone/ligament/ disc compressing the nerve. It can also be accomplished indirectly by mechanically increasing the intervertebral height with an intervertebral interbody spacer or interlaminar spacer, thereby restoring neural foraminal height and reducing the bulging of the ligaments/disc that bulge into the spinal canal centrally.

Restoring natural alignment of the spine: One of the newer paradigms in spinal fixation and fusion, is the restoration of sagittal balance with intervertebral spacers that restore natural lordotic curvature of the spine. The restoration of neutral spinal alignment enables the patient to walk or stand with good posture rather than leaning forward. This reduces the strain on the paraspinal musculature in the spine. Not restoring natural spinal alignment which performing spinal fixation often results in "flat back syndrome" where patients have chronic lower back pain due to muscular fatigue. Additionally inducing natural sagittal balance with the use of lordotic spacers has become a mainstay in preventing degeneration at the adjacent intervertebral spaces above and below a spinal fusion.

Vertebral interbody spacers have become an important part of spinal fixation for reasons which relate to the fundamentals of treating back pain and nerve pain as follows:

Intervertebral spacers improve treatment of mechanical instability: The insertion of an intervertebral spacer provides for more anterior support in fixation of the spine. This helps stabilize mechanical instability. Some intervertebral spacers with large footprints can be used as standalone fixation devices. They can also be used in conjunction with posterior spinal fixation, as they add anterior column supports allowing for more rigid stabilization which prevents hardware loosening and failure of fusion.

Intervertebral spacers improve treatment of nerve root compression: Intervertebral spacers are used to increase the height of a collapsed and degenerated intervertebral disc space. This allows for indirect restoration of height of the associated neural foramina which can relieve compression of the spinal nerve root exiting at that vertebral level. Additionally increasing the height the intervertebral disc space restores a tension to collapsed and bulging ligaments in the spinal canal, namely the PLL and ligamentum flavum. Restoring tension to these ligament through distraction, termed ligamentum taxis, reduces the bulging of these ligaments into the spinal canal. The combination of decompression of the neural foramina and spinal canal reduces radicular sciatic pain and improves neurogenic claudication.

Intervertebral spacers improve restoration of the natural alignment of the spine: When the spine falls out of neutral global alignment, which predominantly refers to being hunched forward or out of sagittal alignment, the patient will experience muscular pain and the back strains throughout the day in attempt to force the patient into a more neutral posture. The lumbar spine has built in natural lordosis which allows us to stand in an upright neutral position. As our discs degenerate, thin, and collapse in height, the lumbar spine often loses that lordosis which is why you see older patients with degenerated spines hunched forward. The popularity of intervertebral spacers has been driven by the face that restoration of disc height or anterior column height can help bring a patient's spine into a more neutral or lordotic position. In this way you can achieve harmony of spinal balance with a fusion. In fact, there has been a rise in use of lordotic and hyperlordotic intervertebral spacers which further induce lordosis in the lumbar spine to help compensate for the kyphosis at other degenerated levels. Fusing a spine without the use of intervertebral spacers in the past often resulted in spinal fixation in a flat or kyphotic position which can leave a patient in chronic pain, termed "flat back" syndrome. Fusing without the use of intervertebral spacing is slowly becoming antiquated. There also currently no existing percutaneous interbody system that allows for specified lordotic correction in the spine. The percutaneous systems that exist today just enable parallel distraction of the disc space.

Interbody fusion implants can be placed into the disc space through either posterior, lateral, or anterior approach trajectories. The two posterior approaches are a posterior lumbar interbody fusion (PLIF) where an interbody fusion implant is placed through a laminectomy, and transforaminal lumbar interbody fusion (TLIF) where the facet joint is resected and the interbody fusion implant is placed through a postero-lateral trajectory. A lateral approach to the spine for placement of an interbody fusion implant is termed lateral lumbar or extreme lateral lumbar interbody fusion (LLIF/XLIF). The two anterior approaches to the lumbar spine are a directly anterior open approach, termed anterior lumbar interbody fusion (ALIF) or an antero-lateral approach, termed oblique lumbar interbody fusion (OLIF). All of these approaches with the exception of the ALIF can be performed through either an open or minimally invasive approach using retractors. The approaches are depicted by FIG. 1. Current percutaneous interbody fusion implants utilize an oblique postero-lateral approach with similar trajectory to a TLIF, but necessitate a slightly more lateral trajectory to get under the facet joint, targeting Kambin's triangle, as one does not typically remove the facet with these approaches but rather they dilate over the disc space in Kambin's triangle.

The drawback with insertion of interbody cages is that there is still a significant amount of dissection and tissue trauma with open or minimally invasive open approaches to gain access to the disc space which equates to more post-operative pain and longer recovery. The advent of more minimally invasive retractors allow for less tissue trauma, but they still involve tissue retraction which can result in non-trivial post-operative pain. Also, the current approach with more minimally invasive retractors is to use smaller interbody implants that fit through the access port. However, a drawback of using smaller implants is that there is less contact surface area with the vertebrae above and below, leading to poor support which increases the risk of subsidence of the implant itself into the adjacent vertebrae. Percutaneous approaches to the spine with tubular dilators are an approach used to even further limit tissue dissection and retraction, but adoption has been limited due to poor visualization of the exiting nerve at Kambin's triangle, and the risk of nerve injury when trying to dilate within a collapsed foramen where the safe zone of Kambin's triangle is even narrower. FIG. 2 is an illustration of Kambin's triangle, which is an approach taken for current endoscopic or percutaneous approaches to the spine. Additionally, current percutaneous techniques are unfamiliar to a lot of surgeons requiring additional training and the unfamiliarity can often increase procedure time.

Current development in interbody fusion devices and techniques, in addition to minimizing the approach, have also focused on the restoration of disc height and lordosis to restore spinal alignment. Existing open and minimally invasive techniques employ the use of instrumentation such as rasps, currettes, shavers, and dilators to clear the disc space and release the vertebral body ligamentous attachments to enable distraction of the intervertebral space. A lot of these instruments when used in an endoscopic or minimally invasive approach are hindered by the inability of the system instrumentation to enable the surgeon to prepare the disc space adequately for the deployed geometry of the implant since access is constrained during the procedure.

There are a number of existing choices of interbody fusion devices. Original interbody fusion devices were static PEEK or metal cages. To enable for improved lordotic correction, these static cages were either shaped with built in lordotic angulation or were inserted and packed on the anterior most portion of the vertebral body and screws were compressed posteriorly to induce lordosis. The drawback of both static and expandable posteriorly inserted cages however, remains that they often subside due to their small footprint and/or contact surface area on the vertebral endplate along with the fact that they don't conform to the vertebral body well which leads to point loading and endplate fracturing. Expandable cages especially are more susceptible to causing endplate fractures as expansion at the anterior wall can create lordosis, but it can also reduce the overall contact surface area by lifting the vertebrae away from the more posterior portions of the rigid implant structure.

While lateral and anteriorly placed cages do possess more surface area and thereby have improved endplate coverage, they still engender a separate incision and dissection for the approach. Currently endoscopically inserted interbody fusion devices can expand height.

Lumbar intervertebral fusion devices are indicated for use in skeletally mature patients with DDD at one or two contiguous levels from L2-L5. DDD is defined as back pain of discogenic origin with degeneration of the disc confirmed via history and radiographic studies. Patients with DDD can also have up to Grade I spondylolisthesis at the involved level(s). Intervertebral devices are indicated to be used with a supplemental fixation system and autograft bone. Intervertebral fusion devices aim to restore disc height and lumbar lordosis; there are several methods of insertion for these devices, with limitations varying across the different approaches to insertion. All insertion methods adopt either an anterior or posterior approach, where anterior insertion entails a greater risk for complications, but accomplishes superior restoration of height and lumbar lordosis.

Due to the nature of the incisions and complications involved with anterior methods of insertion of intervertebral devices, surgeons are gravitating towards posterior methods of insertion. Specifically, the Transforaminal Lumbar Interbody Fusion (TLIF) approach has come to dominate the field of interbody fusion. With insertion at a posterior-lateral angle, comes a limitation to the footprint size. A small window of insertion limits the size of an interbody. A method of circumventing this limitation, employs expandable methods by which to increase footprint after insertion.

The interbody devices described herein can adopt a shape and expansion that can increase the contact points and contact surface area between the vertebral endplate and device in order to more evenly distribute compressive forces exerted on the interbody device. By increasing contact between the vertebral endplates and interbody device, incidences of subsidence can be effectively reduced. Increasing contact can mean increasing contact surface area, increasing distance between contact points, increasing contact with more rigid parts of anatomy, increasing conformity of contact, and more. Expansion can also allow engagement with the peripheral area of the vertebral endplate while minimizing the required entry window to reduce procedure invasiveness. Engaging the peripheral of the vertebral body can allow distribution of forces near the more compact and dense cortical bone. Furthermore, by distributing compressive forces across a greater surface area of the vertebral endplate, migration is reduced. Greater contact with native bone structure promotes better bone fusion, and therefore reduces the likelihood for revision surgery due to interbody failure.

The devices described herein can employ an expandable footprint, adjustable height, and/or adjustable lordosis. By allowing for multiple degrees of adjustment, disc height can effectively be restored and load bearing configuration optimized while minimizing complications and need for revision surgeries. The devices described herein can employ expansion of footprint(s), height, and/or lordosis. The devices described herein can increase surface area that aims to increase the number of contact points resultant surface area of contact.

Geometry of the devices described herein can conform to the geometry of vertebral endplates, with a domed shape defining the contour profile of the expanded superior surface of the device and a flat surface defining the inferior surface of the device

SUMMARY

Interbody systems and methods of using the same are described herein.

The interbody systems described herein have the ability to perform the procedure (disc preparation, implant delivery, implant deployment/expansion, implant final conformation locking and disconnection and instrument withdrawal) through minimally invasive or percutaneous access. In some embodiments, the interbody systems allow access through the following approaches, such as, but not limited to, posteriorly via a laminectomy, a transforaminal approach through resection of facet or through Kambin's triangle, through the superior endplate just below Kambin's triangle, a transpedicular approach with access through the endplate, through a lateral approach, or through other approach trajectories enabled by minimally invasive access. These approaches are depicted by FIG. 1.

In some embodiments, the interbody systems described herein can be configured to perform disc preparation. The remaining disc between the vertebrae can be resected or cleared to enable decompression of the disc space and placement and deployment of an interbody implant. Instrumentation used for disc preparation can be configured to fit through the minimally invasive access window. The systems can be configured to allow for directional clearance of soft tissue. In some embodiments, the systems can also be configured to allow for an annulectomy to further enable distraction of the intervertebral space.

FIG. 7 illustrates disc space distraction 100 using balloon 102. Disc distraction 100 utilizes balloon 102 to compact or break annulus 104 as illustrated by FIG. 8. The balloon can be a high pressure balloon. In some embodiments, the balloon can expand to restore foraminal height as depicted by FIG. 9. The balloon can expand to maximize contact surface area with vertebral end plates as shown in FIG. 10.

In some embodiments, the disc space often needs to be distracted to restore space between the vertebrae to both increase foraminal height, as depicted in FIG. 9, and to create lordosis. The systems described herein are able to deliver sufficient force through the minimally invasive access port to expand the space against any connective tissue that can be connecting the vertebrae. Additionally, the distraction method minimizes point loading to prevent endplate fracture through better contact surface area. The system provides user feedback to alert the user when the vertebral bodies are sufficiently distracted or when then the ligamentous connections between the vertebral bodies are disrupted as depicted in FIG. 14. Such feedback can be in the form of a display of pressure. Distraction can be directional, allowing for selective distraction of the anterior half vs. posterior half of the interbody space (as illustrated in FIGS. 13 and 15).

Sizing of implant. A "trial" system can measure the optimal desired size of the implant through a minimally invasive access port with the aid of fluoroscopy and/or pressure feedback. The system is able to size optimal height, width, and lordotic angle with this percutaneous "trial" method. Optimal sizing can be determined by a measured volume of expansion that produces a desired pressure reading. Optimal sizing can also be determined by conformation of the implant to adjacent vertebral body endplates, or desired distraction visualized with radiographic imaging. A trial system can also give feedback to the user to determine when optimal distraction of the space has occurred.

In some embodiments, an interbody implant can be placed/positioned through a minimally invasive access window as depicted in FIG. 16.

Interbody deployment to maximize contact surface area and hold the desired height and lordotic angle of the intervertebral space as shown in FIG. 18. The interbody can be deployed by the user once at the target site past the minimally invasive access window. The interbody can be retractable and reversible.

Interbody deployment can be aided by an internal balloon to push the contacting surfaces of the interbody to conform to the adjacent vertebral body endplates. The interbody implant itself can stabilize the balloon from slippage or increase the strength of the balloon wall itself. A curved trocar can be used to change the angle of implantation to prevent movement of the balloon or implant.

The interbody implant can remain fixed at the deployed location while in the deployed configuration.

The interbody implant can be locked into a final conformational state that remains stable. The interbody implant can also be filled with a material that can provide load bearing properties or enable bony ingrowth.

In some embodiments, the interbody implant can bear the load of the patient.

DRAWINGS

FIG. 4 depicts an expanded configuration in one plane.

FIG. 5 depicts only one plane of structure.

Figure 13:
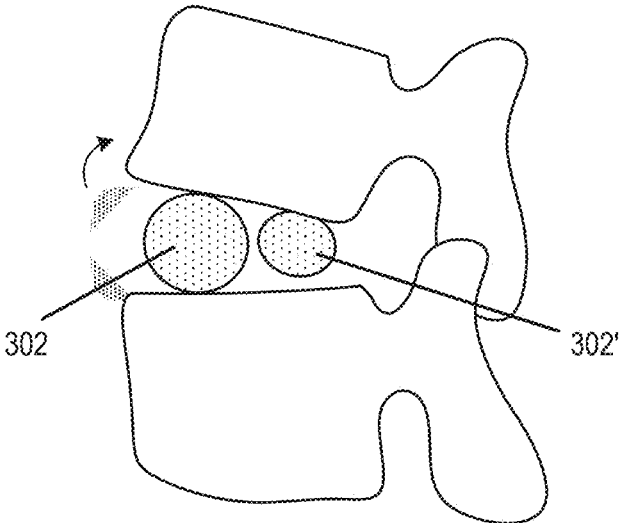

FIG. 13 illustrates the use of multi-chamber balloons to enable selective expansion and/or distraction of the anterior vs. posterior portions of the interbody space. Chambers can be expanded in sync or independently. Expansion shown to create lordosis and break anterior portion of annulus.

Figure 14:
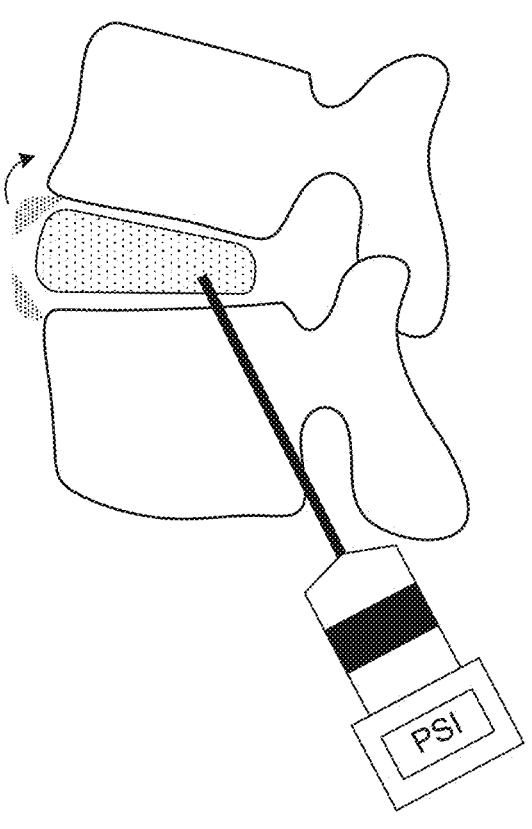

FIG. 14 depicts selective distraction in the anterior portion of disc space to break anterior wall of annulus with instrumentation that includes inflation pressure and/or volume feedback to user. The balloon can be filled with a liquid or gas.

Figure 15:
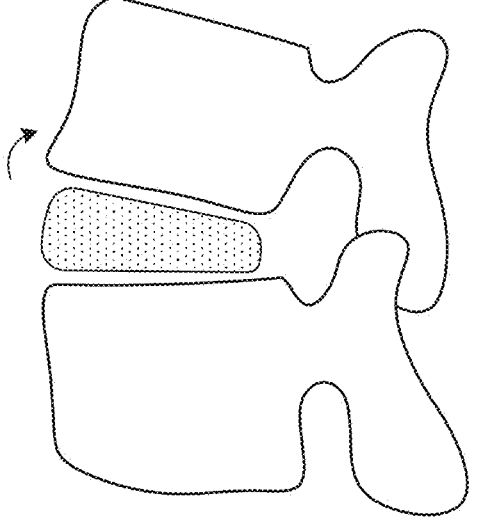

FIG. 15 illustrates a pre-shaped balloon configured to expand more in anterior portion to create lordosis. The balloon is detached and left.

Figure 16:
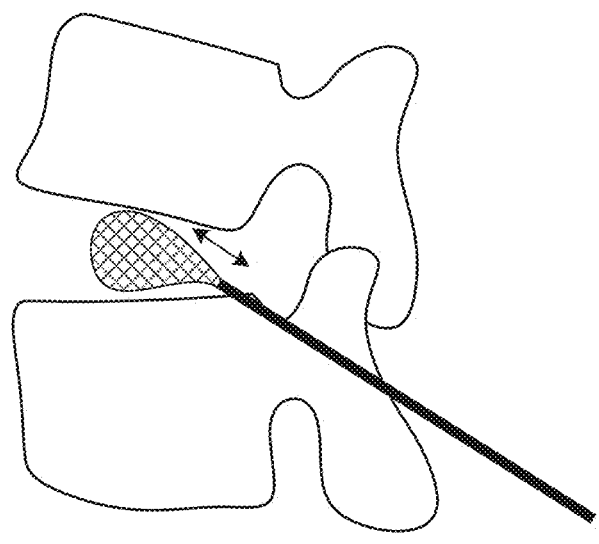

FIG. 16 illustrates an interbody implant placed through a minimally invasive access window after the initial expansion balloon was withdrawn from the space. A containment device that is a webbing is depicted that is also load bearing. The containment device can also be a braid, weave, knit or the like.

Figure 17:
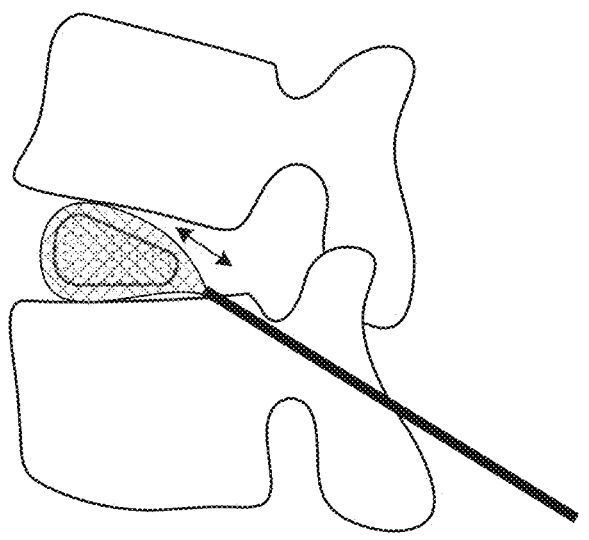

FIG. 17 illustrates a sac containment device that is filled with load bearing filler material.

Figure 18:
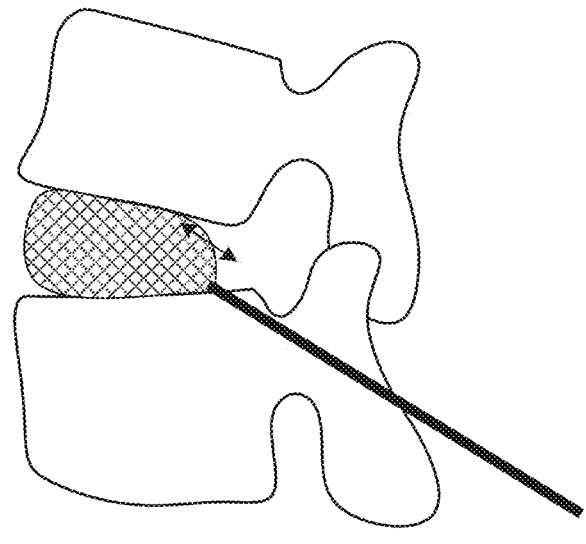

FIG. 18 illustrates an interbody implant deployed to maximize contact surface area and hold the desired height and lordotic angle.

Figure 19:
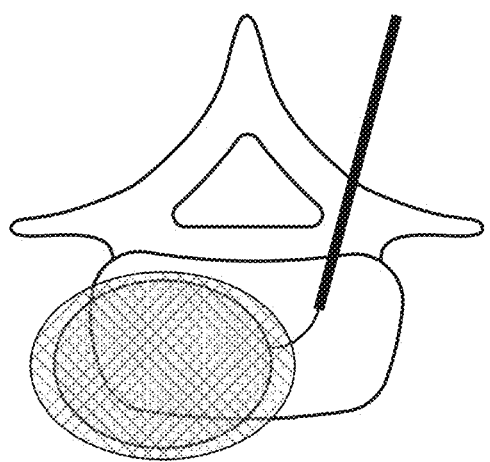

FIG. 19 illustrates an interbody implant being deployed in a trajectory that is off axis of the insertion angle, which prevents slippage of implant back out through the access trajectory.

Figure 20:
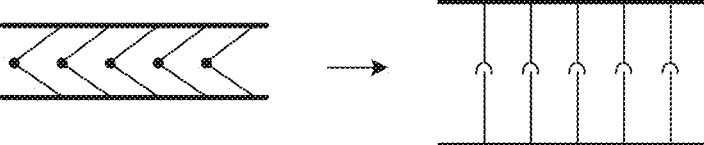

FIG. 20 illustrates an expanding scaffolding structure that locks into place. This is an example of a locking mechanism.

Figure 21:
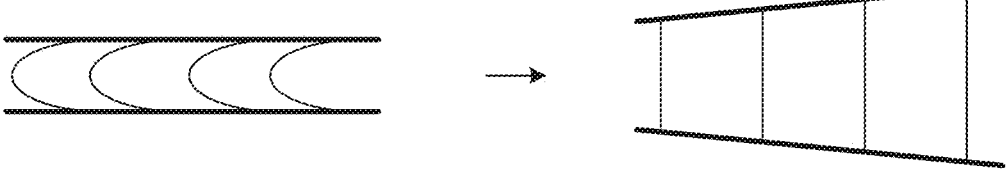

FIG. 21 illustrates a structure that is initially bent tubules that are compact that can expand to straightened tubules.

Figure 22:
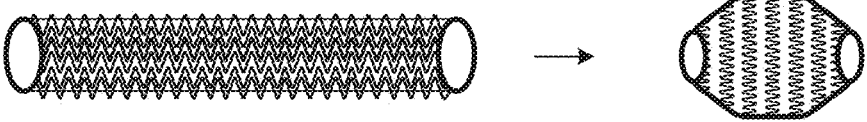

FIG. 22 illustrates mesh that is elongated for delivery that expands into a longitudinally shortened but radially expanded state.

Figure 23:
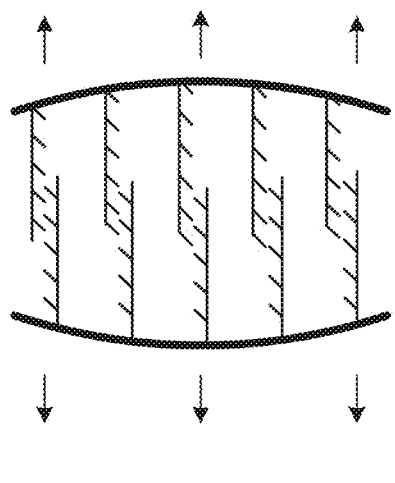

FIG. 23 illustrates a load bearing structure deployed by pump to further expand disc space with fixation mechanisms.

Figure 24:
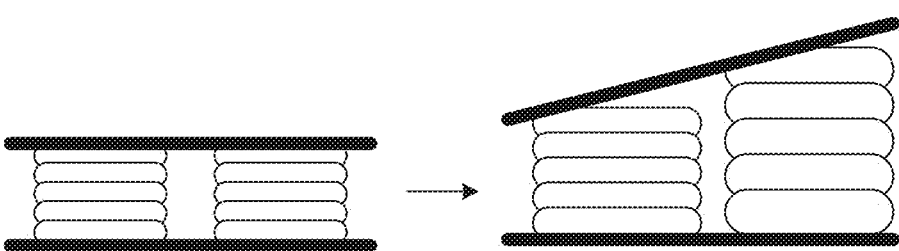

FIG. 24 illustrates multiple balloons or multi-chamber balloon that enables expansion in multiple direction to pre-configured geometry or adjustable geometry.

Figure 25:
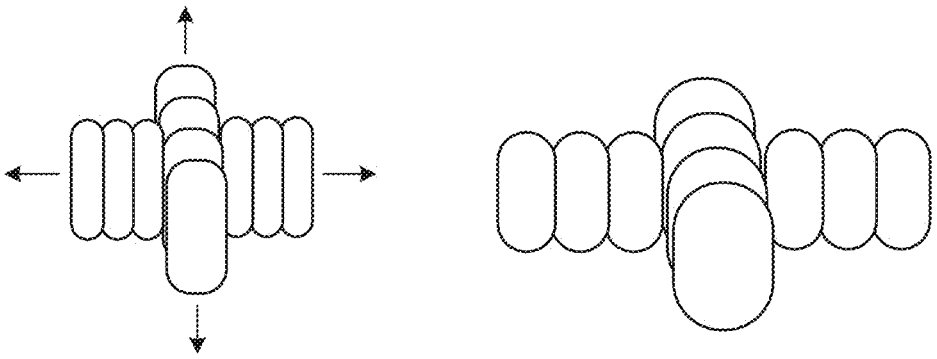

FIG. 25 illustrates multiple expansion mechanisms that enable expansion in different directions.

Figure 26:
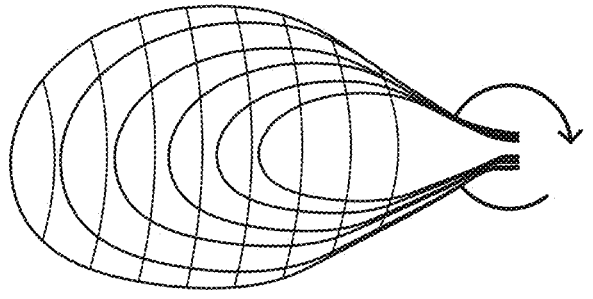

FIG. 26 illustrates the twisting end of the containment device as a closing mechanism.

Figure 27:
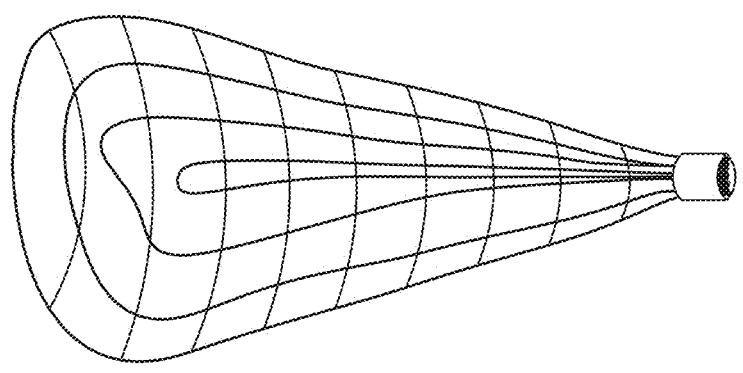

FIG. 27 illustrates the crimping end of the containment device as a closing mechanism.

Figure 28:
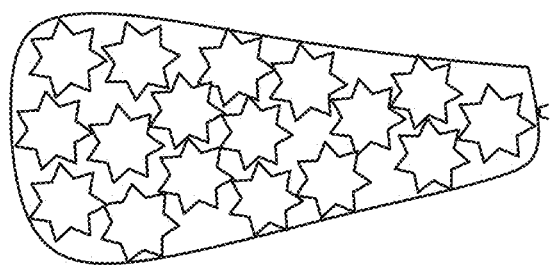

FIG. 28 illustrates a containment device filled with larger interlocking particles that create bigger porosity and trabeculation.

Figure 29:
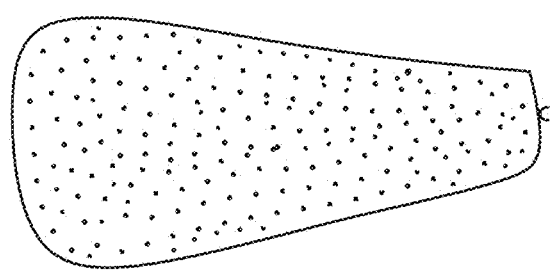

FIG. 29 illustrates a containment device filled with smaller particles that create smaller porosity and trabeculation.

DETAILED DESCRIPTION

Prior to insertion, the devices described herein can exist in a collapsed state that minimizes overall footprint, height, and lordosis. Once a disc is resected, or an insertion path is created, the device can be inserted using a specialized driver that allows for manipulation of insertion angles. Once the tool is inserted within the disc space, the driver can be used to expand the device to a desired height, lordosis, and/or footprint. An additional method can be used to open the vertebral disc space while the device is expanded. An expandable footprint can increase contact points and increase peripheral contact with the vertebral endplates, thereby distributing compressive forces and reducing probability of failure. Furthermore, a greater amount of contact points can promote a greater extent of bone fusion, thereby minimizing risk of cage migration.

The terms "interbody," "interbody device(s)," and "interbody implant(s)," are used interchangeably throughout the specification. In some embodiments, the interbody device can be a stent.

Example Embodiment 1: Hydraulic Bone in a Bag

This embodiment involves a collapsed structure attached to a mesh enclosure. Upon insertion, the device is locked in as it is expanded within the disc space using a hydraulic mechanism such as fluid or gas filled balloons. Once desired expansion is met, the mesh is filled with bone graft until it meets the vertebral endplate increasing contact area.

Example Embodiment 2: Tapered Insertion Geometry with Aided Disc Expansion

This embodiment utilizes a tapered geometry in multiple planes at the leading edge of the device to reduce insertion force needed. The device is comprised of multiple bodies. Upon insertion, vertebral disc space is opened using a hydraulic mechanism such as, but not limited to, fluid filled balloons. Superior body is expanded about pivot and locked in position when desired height and lordosis is met. Bodies may be attached to mesh that is filled with bone graft until mesh contours to the vertebral endplate increasing contact area.

Example Embodiment 3: Matrix Structure

This embodiment involves a structure with multiple cells. The cells are formed with a plurality of connecting branches. In the collapsed condition, the structure is nested in a condensed form. The structure contains an additional body that contacts multiple cells. Upon insertion, the additional body is mechanically engaged with the structure to expand the structure and is locked in place. Structure is expanded until cell connections contact the vertebral end plates at multiple contact points thereby distributing compressive forces.

Example Embodiment 4: Peacock Tail

This embodiment involves expansion about a pivot where multiple bodies rotate to expand footprint(s). When in a collapsed configuration, bodies can be nested together and upon insertion can spread open to create one large structure. This structure can increase surface area of contact, promoting better bone fusion and stability by engaging greater portions of endplates.

Example Embodiment 5: Nested Scaffold

This embodiment involves an expansion method where multiple bodies are nested within one another during a collapsed state, in a fashion similar to a Russian doll. Upon insertion, pieces located within the parent piece can be extracted out and locked into an expanded conformation, so as to increase the contact surface area.

Example Embodiment 6: Deployment of Plates Prior to Insertion of Structure

This embodiment expands the vertebral disc space, prior to insertion of interbody device with a temporary method. Insertion of endplates coupled with an expansion mechanism can increase stability of restored disc height and establish greater number of contact points, therefore, evenly distributing compressive forces.

Example Embodiment 7: Build Up

This embodiment involves adding multiple pieces of identical dimensions to an initial piece, after placement of initial piece is accomplished. An initial piece is inserted in order to establish positioning, after which additional pieces are added to the originally inserted piece, to increase the surface area of contact and evenly distribute compressive forces exerted on interbody device.

Figures 10, 11:
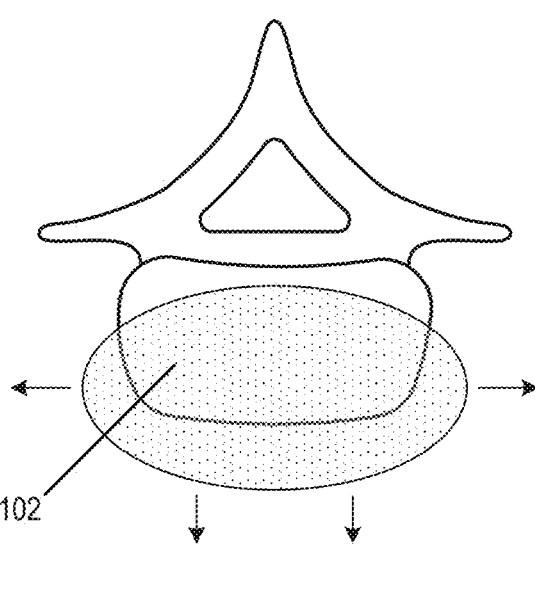
FIG. 10 illustrates disc space clearance and distraction with an expanding balloon to maximize contact surface area with vertebral end plates.
FIG. 11 illustrates a balloon inserted through trocar and pivoted away from the insertion trajectory. The balloon is deployed past the annulus.
Figure 12:
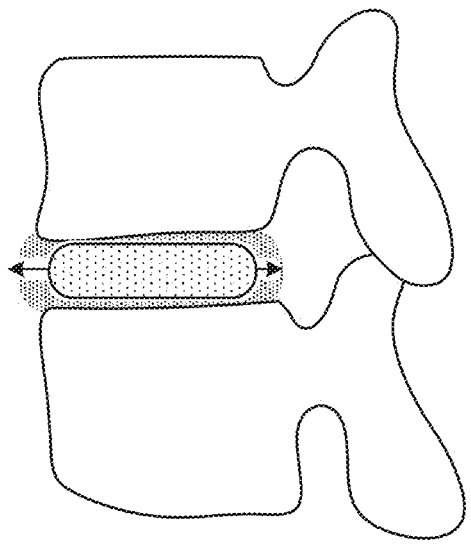
FIG. 12 illustrates expanding a balloon with surface texture to provide friction against slippage that expands and breaks annulus, which enables further expansion.

In some embodiments, the interbody implants (devices) described herein can include a trocar. The trocar can be placed into the target intervertebral space minimally invasively to confirm the trajectory via radiographic imaging as depicted in FIG. 11. In other embodiments, the trocar can inject a dye or tracer solution that permeates part of, or the entire intervertebral space, to allow the surgeon to visualize the space.

In some embodiments, the trocar can also function as an intraoperative nerve monitoring probe or sensor to ensure that the insertion trajectory remains on an acceptable and safe path. The trocar can be attached to a stereotactic system for navigation or fixation point, such as to a pedicle screw or bone, to provide mechanical stability or leverage. In other embodiments, the trocar can have stereotactic fiducials for integration with navigations systems.

The trocar can be curved, steerable or have any shape memory to enable access to the target site in a manner that is not a straight line.

Figure 1:
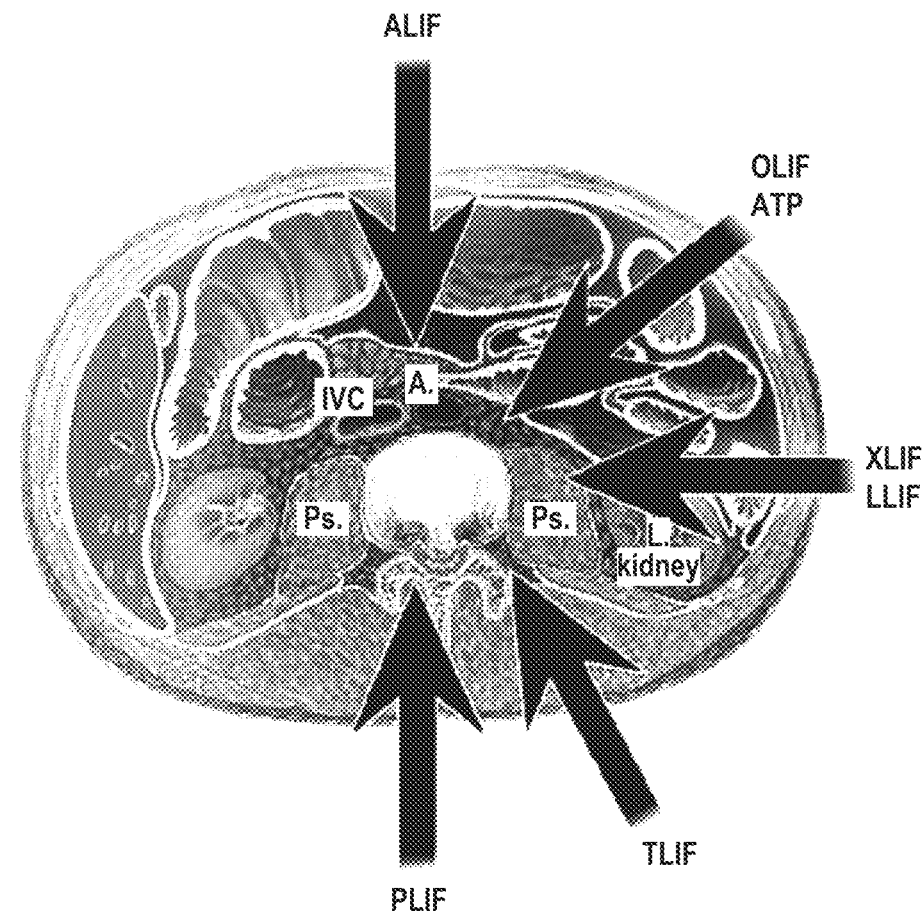
FIG. 1 depicts all posterior, postero-lateral, lateral, antero-lateral, and anterior approaches to the spine for insertion of vertebral interbody devices.
Figure 2:
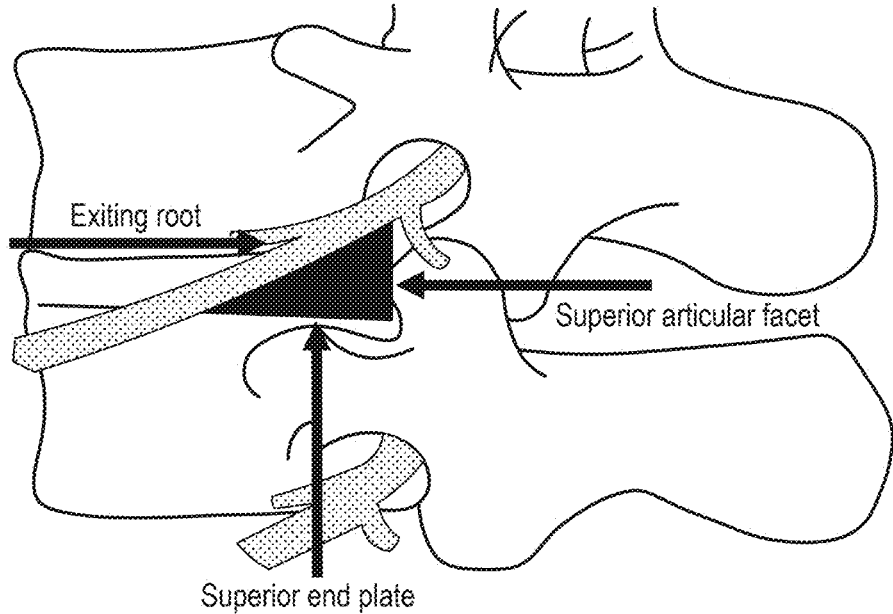
FIG. 2 is an illustration of Kambin's triangle.
Figure 3:
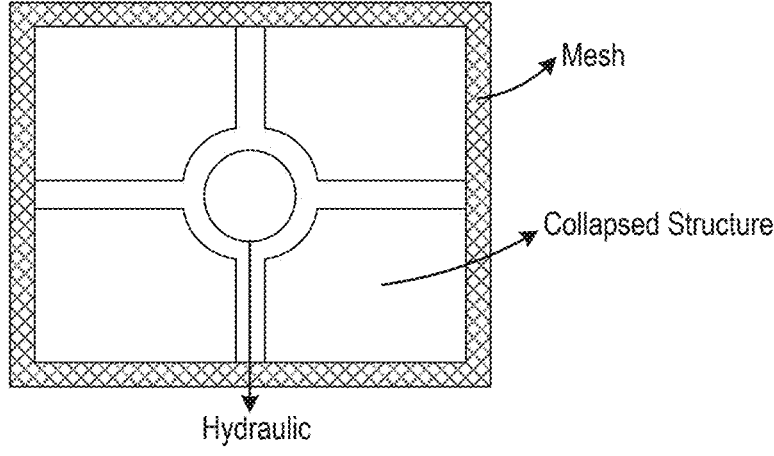
FIG. 3 illustrates an example embodiment of the systems described herein, namely Example Embodiment 1, a structure coupled with mesh. The figure depicts a collapsed condition and an expanded position.
Figure 3:
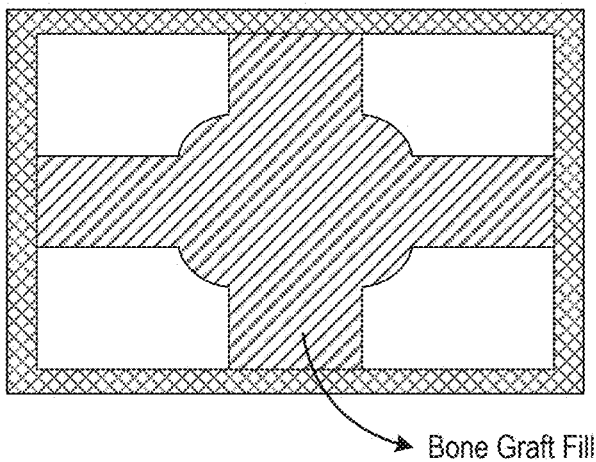
Figure 4:
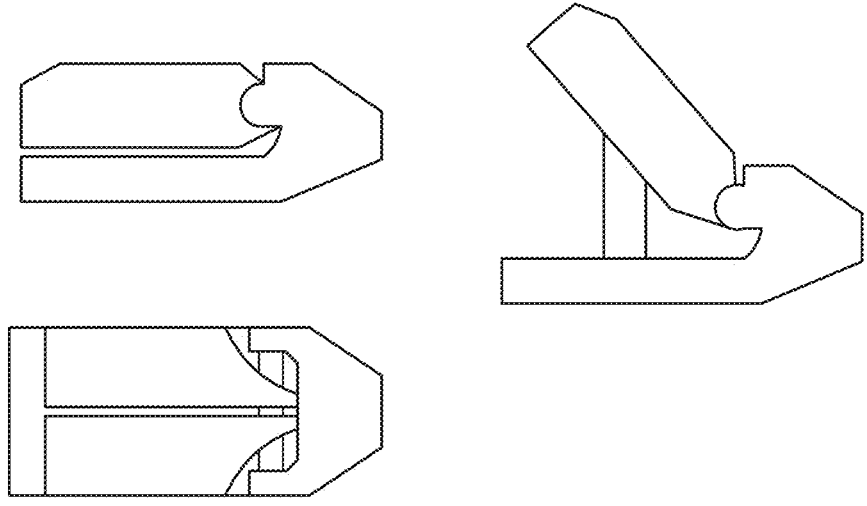
FIG. 4 illustrates an example embodiment of the systems described herein, namely Example Embodiment 2, a structure with a tapered leading edge.
Figure 5:
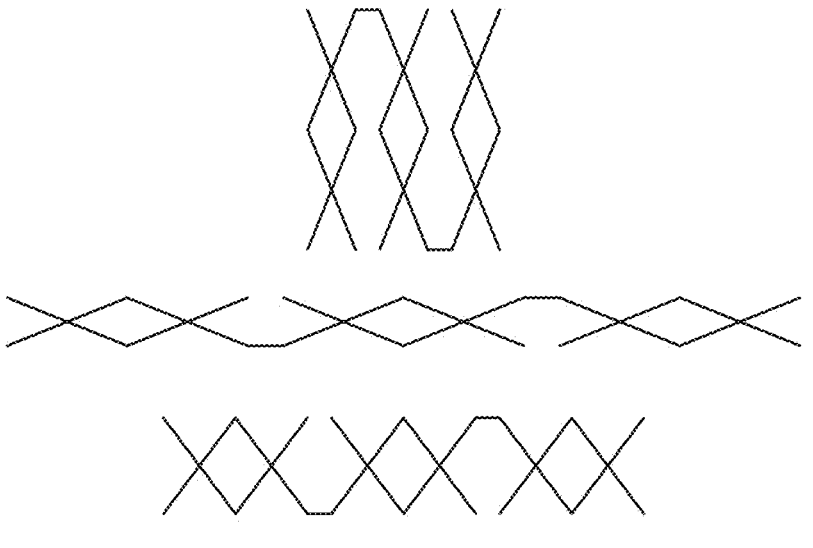
FIG. 5 illustrates an example of a matrix structure in an insertion configuration transitioned to an expanded configuration.
Figures 6, 7:
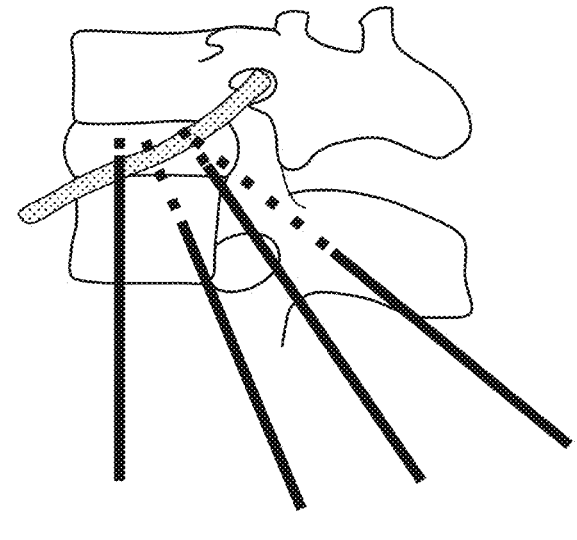
FIG. 6 illustrates an example of approach trajectories and trocar access, which can be visualized under radiographic imaging including the ability to punch through cortical bone. The trocar can have sensors such as, but not limited to, nerve monitoring sensor(s), pressure sensor(s), impedance sensor(s), and the like and/or a combination thereof.
FIG. 7 illustrates an example of disc space distraction utilizing a balloon.
Figure 8:
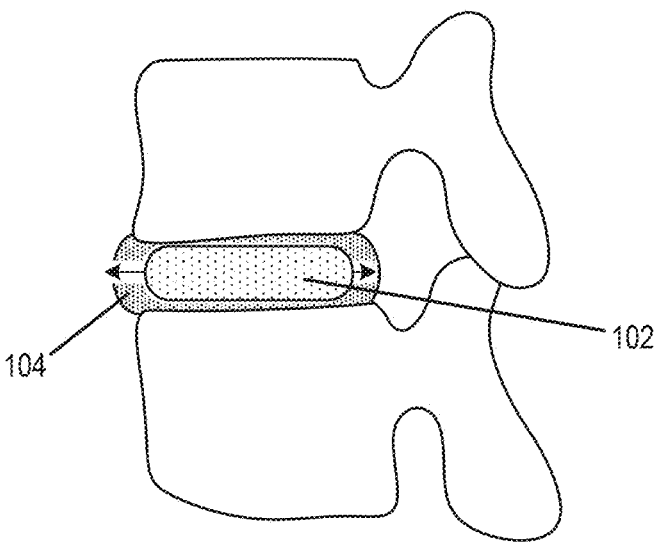
FIG. 8 illustrates an example of disc space distraction utilizing a balloon to compact or break the annulus.
Figure 9:
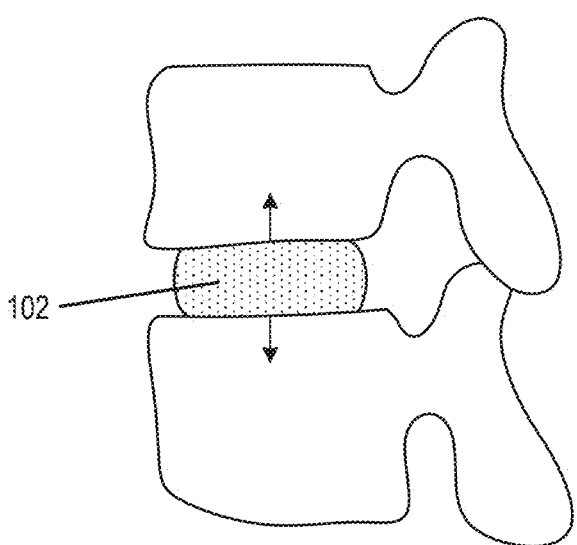
FIG. 9 illustrates an example of disc space distraction with an expanding balloon to restore foraminal height.

In some embodiments, the trocar can have a component or geometry that enables it to punch through cortical bone as depicted in FIG. 6. In other embodiments, the trocar can have a geometry that would enable access through a superiorly pointed transpedicular approach to gain access to the disc space through the endplate of the vertebral body. In some embodiments, the trocar can have a geometry that enables access through a lateral or oblique lateral approach, where the trocar can enter the disc space under Kambin's triangle through the lateral vertebral body wall and superior endplate under Kambin's triangle. In other embodiments, the trocar can have a geometry that enables access through an approach going through the superior articulating process of the facet joint into the disc space.

In some embodiments, the trocar can include one or more sensors which can be used to characterize the type of tissue that the trocar is traversing. The one or more sensors can be, but are not limited to, pressure sensors, impedance sensors, ultrasonic sensors, and the like, and/or a combination thereof.

In other embodiments, the trocar can have a shim bullet nose geometry allowing for it to bluntly gain access into a tight disc space without violating the endplate or having a sharp edge that may inadvertently cut dura.

In other embodiments, the trocar can employ a mechanism to prevent it from backing out. This mechanism can include expansion of the radius of the distal end. Alternatively, the trocar can couple to a screw anchor mechanism that anchors it to the bone it traverses.

In some embodiments, the interbody devices described herein can include disc preparation instrumentation that can be used to sever, cut or resect tissue or bone in the disc space through the minimally invasive access trajectory. Disc preparation instrumentation can include, but is not limited to, augers, drills, cutters, biters, scrapers, punches and the like, and/or a combination thereof. The disc preparation instruments can expand to allow for endplate to endplate contact. The instruments can have steerable working tips. In some embodiments, the tips can be articulating in one or many directions. Steering can be achieved through linkages, gear mechanisms, cable mechanisms, shape memory properties and the like. In some embodiments, the disc preparation instrumentation can be used to expand the disc space.

In other embodiments, the systems can include an expansion balloon, sac, bladder, or the like. The expansion balloon, sac, bladder, or the like can be inserted over the trocar, through the trocar, or by itself through the path created by the trocar as depicted in FIG. 6. The balloon can be used to apply pressure against the connective tissue in the target disc space. In some embodiments, the expansion force can be used to break, stretch or sever connective tissue or bone that is compressing the space. In other embodiments, the expansion force can be used to compact connective tissue or bone to create a void for the implant to be deployed. In some embodiments, the expansion force can be used to shift, move or push connective tissue or bone to make space for the implant to be deployed.

The balloon can include a surface texture to provide friction against slippage. Surface texture, can include, but is limited to, metal wiring on the outer surface, rough surface properties, grates, adhesives and the like.

In some embodiments, the balloon can be deployed within another device that can be used to clear or cut tissue. The instrumentation can pivot the balloon once it is delivered to the target space such that it is no longer in line with the insertion trajectory. This can place the balloon in a more advantageous position for expansion. This can also prevent the balloon from slipping out the insertion path as it encounters opposing force during expansion as depicted in FIG. 11.

In other embodiments, the balloon can include one or more sensors to indicate its deployment status, provide feedback to the surgeon or control system feedback for safety as depicted in FIG. 14. In some embodiments, the sensor(s) can be a strain gauge on the surface of the balloon to measure expansion. Multiple strain gauges on the surface of the balloon can determine the three-dimensional expansion direction of the balloon. In other embodiments, the sensor(s) can be a pressure gauge to provide feedback on the experience force or rate of expansion. This can be used as information for the surgeon regarding magnitude of compression. This can also be used to provide a safeguard against overexpansion and potential rupture of the balloon. Sudden drops in pressure can be used to indicate the breakage of connective tissue. In some embodiments, the sensor(s) can be configured for volume measurement which allows for feedback on available disc space size and volume.

In some embodiments, the balloon can be pressurized by gas or liquid. In other embodiments, the balloon is withdrawn from the patient before the next step. In some embodiments, the balloon can be detached and left in the patient before the next step.

The balloon can be radiopaque or filled with radiopaque material so that it can be inflated to conform to the prepared disc space and visualized from radiographic imaging or the like. The balloon or a device connected to the balloon can enable the user to extrapolate the volume of expansion and the height of the anterior, posterior, or lateral borders of the balloon.

The balloon can incorporate multiple chambers that enable expansion in different directions or shapes. FIG. 13 depicts a balloon with multiple chambers 302 and 302'. The balloon can be comprised of one or more chambers. The number of chambers can depend on the different directions and/or shapes desired. In some embodiments, the balloon can be pre-shaped to enable directional expansion or preferential expansion of different sections of the intervertebral space as depicted in FIG. 15. The balloon can be deployed past the annulus laterally or anteriorly as depicted in FIG. 11. The balloon can incorporate multiple chambers that can be expanded together or independently as depicted in FIG. 13.

The systems can comprise one or more load-bearing structures that can be deployed at the target site following space preparation. The use of an expansion balloon prior to deploying the load bearing structure enables the use of structures that have small expansion forces, but large static load bearing forces when deployed. One example is an expanding scaffolding structure that locks into place to bear static forces is depicted by FIG. 20. The lock can be a ratcheting mechanism, catching mechanism, engagement of pins or the like, and/or a combination thereof. Another example is a structure made of shape memory that is initially bend tubules to form a compact, collapse form for insertion that recovers to straightened tubules to provide strong static load bearing capability as depicted by FIG. 21. Another example includes a permeable mesh having a proximal end, a distal end, and a radially constrained elongated state configured for delivery within a catheter lumen or trocar, an expanded state with a longitudinally shortened configuration relative to the radially constrained state, and a plurality of elongate filaments that are woven together to form a mesh as depicted by FIG. 22.

While the use of an expansion balloon reduces the expansion force needed to deploy the load bearing structure, the deployment of the load bearing structure can also continue to expand the disc space. The deployment of the load bearing structure can be used to drive fixation mechanisms to the vertebrae above and below the space. In some embodiments, the fixation mechanism can include nail(s), screw(s), spike(s), grate(s), webbing, grit texture or the like at the interface surfaces to the vertebral end plates. The expansion force can be used to dig these fixation features into the adjoining connective tissue and/or bone. The expansion means can be a pneumatic mechanism, hydraulic mechanism, mechanical mechanism, shape memory mechanism, gas expansion mechanism via chemical reaction or thermal expansion and the like.

An alternative or adjunct to deploying a load bearing structure can be to deploy a containment sac, webbing, braid, weave, knit, balloon or the like and to fill said containment device with a load bearing filler material. Using a containment device that conforms to the disc space and the adjoining vertebral endplates can maximize the load bearing surface area. Some advantages of this include more durability, reducing or preventing subsidence and the like. The containment device can be load bearing on its own or can be filled with load bearing filler material as depicted in FIG. 17. The containment device can have a closure mechanism after filling is complete as depicted in FIG. 24. The closure mechanism can be a cap, crimping the open end shut, twisting a malleable portion to close, adhesives, a screwcap, and the like, and or a combination thereof.

In some embodiments, load bearing structures and/or containment devices can be filled with material. The material can be load bearing filler material to provide additional load bearing capability. Filler material can be, but is not limited to, liquid, gas, solids, particles or the like with various properties, and/or a combination thereof. The material can include properties such as, but not limited to, compressive force, tensile force, adhesion, promoting bone ingrowth, phase change, hardening and/or a combination thereof. Filler materials can be, but are not limited to, cement, demineralized bone putty, epoxy, rigid particles, small metal particles, bone fragments, and/or a combination thereof. Some fillers such as, but not limited to, cement, epoxy and putty can allow pressurized injection, which can be controlled to reach a certain pressure to ensure that it is bearing load. Fillers that are liquid-like can remain a liquid or cure, set, or harden into a more solid-like structure. Fillers that are smaller particles such as, but not limited to, demineralized bone, sand-like particles such as biomaterials, silica particles, ceramic particles, metal particles, bone particles, and/or a combination thereof can be tamped and packed to ensure a bearing load as depicted by FIG. 28. Similarly, larger rigid particles can be tamped and packed into the containment device. When these larger rigid particles are packed together, their physical features can interlock to break a rigid structure as depicted by FIG. 23. A combination of different types of filler materials can be used. With use of curative agents, a relatively longer cure time can enable intra-procedural removal of the implant such as on the order of one to two hours.

One feature of a different configuration of filler materials is the resulting porosity and trabeculation of the load bearing materials. Smaller filler material particles lead to denser bulk with less porosity. Larger filler material particles lead to less dense bulk with larger porosity. Various combinations of particle size can be used to achieve desired densities and porosity.

Filler materials or additives can also have additional properties to promote bony ingrowth. In some embodiments, BMP2, collagen, hydroxyappetite, or others, or combinations of such additives can be used. In other, embodiments the filler material has inherent properties that promote bony ingrowth such as tantalum surfaces and the like.

In some embodiments, a method of deploying an interbody implant into a vertebral disc space comprises inserting an inflatable balloon into the vertebral disc space wherein the inflatable balloon is configured to expand into the vertebral disc space thereby clearing the vertebral disc space; expanding the inflatable balloon to restore foraminal height; withdrawing the inflatable balloon from the vertebral disc space; guiding the interbody implant through a minimally invasive access window into the vertebral disc space; and deploying the interbody implant into the vertebral disc space.

The interbody implant can be an expansile filament. In other embodiments, the trocar is attached to an additional fixation point affixed to bone. The additional fixation point can be a pedicle screw. In some embodiments, the trocar is curved. The trocar can be inserted laterally or posteriorly. In other embodiments, the inflatable balloon further comprises an outer sleeve. The outer sleeve can include a rough surface to enable disc clearing and further expansion.

In some embodiments, the interbody system further comprises one or more load-bearing structures. There can be 1, 2, 3, 4, or more load-bearing structures. The one or more load-bearing structures can be filled with load bearing material. Load bearing material can include, but is not limited to, cement, demineralized bone putty, epoxy, rigid particles, small metal particles, bone fragments, or a combination thereof.

In other embodiments, the trocar further comprises one or more sensors. Theone or more sensors can be a pressure sensor, an impedance sensor, an ultrasonic sensor, or a combination thereof. In some embodiments, interbody implant can include a closing mechanism. The closing mechanism can prevent extrusion of inner material. The closing mechanism can be a mechanical crimp, an electrostatic closure, a screw cap, a plug, or a combination thereof. In other, embodiments the inflatable balloon can be inserted onto a trocar, in a trocar, or over a trocar. In some embodiments, the inflatable balloon can be configured to attach to the trocar in a desired configuration for expanding and/or clearing the vertebral disc space.

In some embodiments, a method of implanting an interbody implant into a vertebral disc space comprises inserting an inflatable balloon into the vertebral disc space wherein the inflatable balloon is configured to expand into the vertebral disc space thereby clearing the vertebral disc space; expanding the inflatable balloon to restore foraminal height; withdrawing the inflatable balloon from the vertebral disc space; guiding the interbody implant through a minimally invasive access window into the vertebral disc space; and implanting the interbody implant into the vertebral disc space.

In some embodiments, expansion of the vertebral space can in the range of between about 0 degrees to about 30 degrees, between about 0 degrees to about 10 degrees, between about 0 degrees to about 20 degrees, between about 10 degrees to about 20 degrees, between about 10 degrees to about 30 degrees, between about 20 degrees to about 30 degrees, 0 degrees, 1 degrees, 2 degrees, 3 degrees, 4 degrees, 5 degrees, 6 degrees, 7 degrees, 8 degrees, 9 degrees, 10 degrees, 11 degrees, 12 degrees, 13 degrees, 14 degrees, 15 degrees, 16 degrees, 17 degrees, 18 degrees, 19 degrees, 20 degrees, 21 degrees, 22 degrees, 23 degrees, 24 degrees, 25 degrees, 26 degrees, 27 degrees, 28 degrees, 29 degrees, 30 degrees, about 0 degrees, about 1 degrees, about 2 degrees, about 3 degrees, about 4 degrees, about 5 degrees, about 6 degrees, about 7 degrees, about 8 degrees, about 9 degrees, about 10 degrees, about 11 degrees, about 12 degrees, about 13 degrees, about 14 degrees, about 15 degrees, about 16 degrees, about 17 degrees, about 18 degrees, about 19 degrees, about 20 degrees, about 21 degrees, about 22 degrees, about 23 degrees, about 24 degrees, about 25 degrees, about 26 degrees, about 27 degrees, about 28 degrees, about 29 degrees, about 30 degrees. In other embodiments, the range of degrees can be prior to deploying/implanting the interbody implant. In some embodiments, the range of degrees can be after deploying/implanting the interbody implant.

In other embodiments, a method of deploying an interbody implant into a vertebral disc space comprises inserting an inflatable balloon into the vertebral disc space wherein the inflatable balloon is configured to expand into the vertebral disc space thereby expanding the vertebral disc space; expanding the inflatable balloon to restore foraminal height; withdrawing the inflatable balloon from the vertebral disc space; guiding the interbody implant through a minimally invasive access window into the vertebral disc space; and deploying the interbody implant into the vertebral disc space.

In some embodiments, an interbody system comprises an interbody implant including an expansion balloon; and a trocar; wherein the interbody implant is inserted through the trocar. The interbody implant can be expansile filament. In other embodiments, the interbody implant can include a braided structure, a weaved structure, a knit structure, a web-like structure, or a combination thereof. In some embodiments, the interbody system can further comprise an apparatus or apparatuses/instrumentation for disc preparation. Disc preparation can include clearing the space of any tissue and/or expanding the space to create a void for the interbody implant. In other embodiments, the interbody system can further comprise one or more load bearing structure(s).

In some embodiments, the systems described herein are utilized for a spine interbody implant procedural technique. The interbody implant can be an expansile filamentous interbody device. The trocar is advanced into the intervertebral space. The intervertebral space can be confirmed with the injection of dye which should permeate through the empty or degenerated disc space vs. in the vertebral body. For disc spaces this can confirm a tight intervertebral space.

The balloon can be inserted with an angulation to prevent the balloon from backing out through initial trajectory at high pressures given the disc is slippery opposed to bone.

Possible auditory feedback or visual feedback can signal to the operator absolute pressure and rate of pressure change. This can aid the operator in assessing if the disc or all the intervertebral space has "popped."

Intraoperative nerve monitoring on the trochar itself can be useful for percutaneous transforaminal approach through Camdens triangle.

In some embodiments, the trocar can be attached to an additional fixation point affixed to bone (such as, but not limited to, one or more pedicle screw(s) or pars, facet, or lamina) to prevent backing out.

Deploy balloon over a curved trocar with either varying curves or having adjustability of curves to better direct balloon and implant deployment. The purpose of deploying over a curved trocar is to prevent backing up of the lifting balloon and implant.

In some embodiments, insertion of the trocar can be posterior. Posterior can include, but is not limited to, percutaneous or endoscopic via Camden's Triangle, open or MIS Open (tubular approach) after doing hemi-laminectomy, transpedicular, or aimed to go through the superior articulating process.

In other embodiments, insertion of the trocar can be lateral. Lateral can include, but is not limited to, open via lateral retractor with a monitored trocar inserted through the psoas muscle without disrupting it. An advantage of this procedure is that the psoas muscle is not disrupted or torn for disc preparation or insertion because there is no large implant to be pushed through the psoas muscle.

In some embodiments, for second stage after disc clearing an implant with an inner expansion balloon can be deployed to confirm positioning, provide additional expansion, and maintain the expanded position prior to or during filling with cement or demineralized bone putty.

Interbody LIFT Balloon+Disc Preparation

In some embodiments, an inflatable balloon is used to clear a disc space. The inflatable balloon can comprise an outer sleeve over the lift balloon that has a rough surface or grated surface that enables disc clearing with expansion. This can also allow for roughening of the bone without violation of the endplates which would promote fusion. The sleeve can also provide additional friction in a slippery intradiscal space to prevent backout.

In other embodiments, the inflatable balloon can induce angulation in vertebral body orientation via pre-formed dimensions for lordotic/kyphotic correction or correction of coronal misalignment.

In some embodiments, the balloons sides have various sizes to match the endplates or go past the endplates on the sides or front of the vertebral body to loosen or break anterior longitudinal ligament or lateral osteophytes or a shape with a larger anterior height allowing for repositioning of vertebral body alignment.

In some embodiments, the balloon includes attachments that enable directional bone/disc clearance. In other embodiments, the balloon can include a pressure indicator that reads out pressure, and/or rate of increase pressure per cc of fluid to give a rate of pressure change.

In some embodiments, the balloon includes a stereotactic guidance option to be used with stereotactic guidance system or augmented reality platform. There can be radiopacity of the balloon wall or use of contrast dye to visualize deployment.

In some embodiments, there can be a netting of pressure cages as a sleeve over the balloon to provide info for load distribution and direction of expansion. The trocar can have a tapered "shim contour" to help it slide into tight intervertebral spaces.

Endoscopic tools or clearing burrs to enable clearing of disc space with or without attachment to bony instrumentation as a point of fixation.

Spine Expansile Filamentous Interbody Implant with Inner Expansion Balloon

A spine expansile filamentous interbody implant with inner expansion balloon is described herein. The interbody implant can be an implantable filamentous device including a braided structure, a weaved structure, a knit structure, a web-like structure or any other structure that can press fit and integrate with the bone.

In some embodiments, the filamentous interbody device can have inherent properties in the metal that allows for bony ingrowth. In other embodiments, the metal can be surface treated to allow for bony ingrowth, such as, but not limited to, spray deposition of titanium of hydroxyappetite. In other embodiments, the deployable implant can be "sized" and is reversible. The implant can be sized by deploying balloon within the implant to see how it fits and to be comfortable with angulation, size, and alignment.

In some embodiments, the filamentous interbody device is reversible, and can be withdrawn while simultaneously moving filler material out of the intervertebral space.

In some embodiments, the implants can include shapes with larger height anterior edges. In other embodiments, the implants can maximize implant expansion to outer edges of the endplate. In some embodiments, implants can include an inner netting with strain gauges to read out distribution of forces on the implant. The implant can be expanded enough to have an even distribution of load. In some embodiments, the implants are stents.

In some embodiments, the implant can be "closable" following backfill to prevent extrusion of inner material. Other embodiments, can include a mechanical crimp, an electrostatic closure, a screw cap, plug, or other type of closure mechanism.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments become apparent to those of ordinary skill in the art upon reading the foregoing description. The inventor expects those of ordinary skill in the art to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A method of deploying an interbody implant into an intervertebral space of a patient, the method comprising:
   inserting an elongate tube proximate to the intervertebral space;
   inserting an inflatable balloon through the tube and into the intervertebral space;
   expanding the inflatable balloon to apply pressure against anatomy of a target disc space and to restore foraminal height;
   withdrawing the inflatable balloon from the intervertebral space;
   inserting the interbody implant through the tube into the intervertebral space; and
   filling the interbody implant with a load bearing filler material that comprises a plurality of particles configured to interlock to form a load bearing structure in the intervertebral space.

2. The method of claim 1, wherein the trocar tube is attached to a fixation point affixed to bone.

3. The method of claim 2, wherein the fixation point is a pedicle screw.

4. The method of claim 1, wherein the tube is curved.

5. The method of claim 1, wherein the tube is inserted laterally.

6. The method of claim 1, wherein the tube is inserted posteriorly.

7. The method of claim 1, wherein the inflatable balloon further comprises an outer sleeve.

8. The method of claim 7, wherein the outer sleeve includes a rough surface to enable disc clearing and further expansion.

9. The method of claim 1, wherein the load bearing filler material comprises cement, demineralized bone putty, epoxy, rigid particles, small metal particles, bone fragments, or a combination thereof.

10. The method of claim 1, wherein the tube further comprises one or more sensors.

11. The method of claim 10, wherein the one or more sensors is a pressure sensor, an impedance sensor, an ultrasonic sensor, or a combination thereof.

12. The method of claim 1, wherein the interbody implant includes a closing mechanism.

13. The method of claim 12, wherein the closing mechanism prevents extrusion of inner material.

14. The method of claim 13, wherein the closing mechanism is a mechanical crimp, an electrostatic closure, a screw cap, a plug, or a combination thereof.

15. An interbody system for treating back pain and nerve pain of a patient, comprising:
   a tube configured to be inserted into an intervertebral space of the patient;
   a balloon configured to be inserted through the tube, wherein the balloon can be used to apply pressure against anatomy of a target disc space;
   an interbody implant configured to be inserted through the tube; and
   a load bearing filler material configured to be inserted into the interbody implant, wherein the load bearing filler material comprises a plurality of particles configured to interlock to form a load bearing structure in the intervertebral space.

16. The interbody system of claim 15, wherein the interbody implant includes a braided structure, a weaved structure, a knit structure, a web-like structure, or a combination thereof.

17. The interbody system of claim 15, wherein the load bearing filler material comprises cement, demineralized bone putty, epoxy, rigid particles, small metal particles, bone fragments, or a combination thereof.

18. The interbody system of claim 15, wherein the balloon is configured to expand to restore foraminal height.

19. The interbody system of claim 15, wherein the balloon is configured to distract the target disc space to create lordosis.

20. The interbody system of claim 15, wherein the tube is curved.

21. The interbody system of claim 15, wherein the tube has a geometry that enables access through a superiorly pointed transpedicular approach to gain access to a disc space through an endplate of a vertebral body.

22. The interbody system of claim 15, wherein the tube has a geometry that enables access through a lateral or oblique lateral approach, and wherein the tube is configured to enter the target disc space under Kambin's triangle through a lateral vertebral body wall and superior endplate under Kambin's triangle.

23. The interbody system of claim 15, wherein the tube has a geometry that enables access through an approach going through a superior articulating process of a facet joint into the target disc space.

24. The interbody system of claim 15, wherein the balloon is a first ballon, and wherein the interbody implant is configured to be expanded by deploying a second balloon within the interbody implant.

25. The interbody system of claim 15, wherein the interbody implant includes a closing mechanism to prevent extrusion of the load bearing filler material.

26. The interbody system of claim 15, wherein the tube is steerable.

27. A method of deploying an interbody implant into an intervertebral space of a patient, the method comprising:

accessing the intervertebral space via a minimally invasive surgical access path;

inserting the interbody implant into the intervertebral space along the minimally invasive surgical access path, wherein the interbody implant comprises an expandable mesh structure; and inserting a load bearing filler material into the interbody implant via the minimally invasive surgical access path, wherein the load bearing filler material comprises a plurality of particles configured to interlock to form a load bearing structure in the intervertebral space.

\* \* \* \* \*